(12) United States Patent
Marche

(10) Patent No.: US 9,672,661 B2
(45) Date of Patent: Jun. 6, 2017

(54) DAMAGE DETECTION AND REPAIR SYSTEM AND METHOD USING ENHANCED GEOLOCATION

(71) Applicant: AIRBUS OPERATIONS (S.A.S.), Toulouse (FR)

(72) Inventor: Jacques Herve Marche, Toulouse (FR)

(73) Assignee: AIRBUS OPERATIONS (S.A.S.), Toulouse (FR)

( * ) Notice: Subject to any disclaimer, the term of this patent is extended or adjusted under 35 U.S.C. 154(b) by 57 days.

(21) Appl. No.: 14/733,046

(22) Filed: Jun. 8, 2015

(65) Prior Publication Data

US 2016/0358384 A1  Dec. 8, 2016

(51) Int. Cl.
*G06T 19/20* (2011.01)
*G01N 21/88* (2006.01)

(52) U.S. Cl.
CPC ......... *G06T 19/20* (2013.01); *G01N 21/8806* (2013.01); *G01N 2201/12* (2013.01)

(58) Field of Classification Search
CPC ....... G06T 7/001; G06T 19/20; G06T 7/0004; G06T 7/0012; G06T 2207/30108–2207/30164
See application file for complete search history.

(56) References Cited

U.S. PATENT DOCUMENTS

| | | | |
|---|---|---|---|
| 9,045,318 B1* | 6/2015 | Polus ...................... B66C 13/30 | |
| 2010/0164862 A1* | 7/2010 | Sullivan ............... G06K 9/3216 | 345/156 |
| 2012/0140041 A1* | 6/2012 | Burgunder ............. G01B 11/24 | 348/46 |
| 2015/0130840 A1* | 5/2015 | Heinonen ............... G01S 17/08 | 345/633 |
| 2016/0253563 A1* | 9/2016 | Lam ................... G06K 9/00671 | |

* cited by examiner

*Primary Examiner* — Jacinta M Crawford
*Assistant Examiner* — Diane Wills
(74) *Attorney, Agent, or Firm* — Greer, Burns & Crain, Ltd.

(57) ABSTRACT

A damage detection and repair system is provided for performing a damage detection and repair preparation process, and includes an image-capturing device having at least one camera lens, a first positional sensor, and an orientation sensor. At least three second positional sensors are provided for the object to detect a corresponding three-dimensional (3D) position of the object relative to the image-capturing device. A location determination module determines a positional information of the damage of the object based on signals received from the first positional sensor, the orientation sensor, and the second positional sensors. A 3D generation module generates a 3D digital mockup model for illustrating the damage of the object and associated parts needed for repairing the damage.

20 Claims, 5 Drawing Sheets

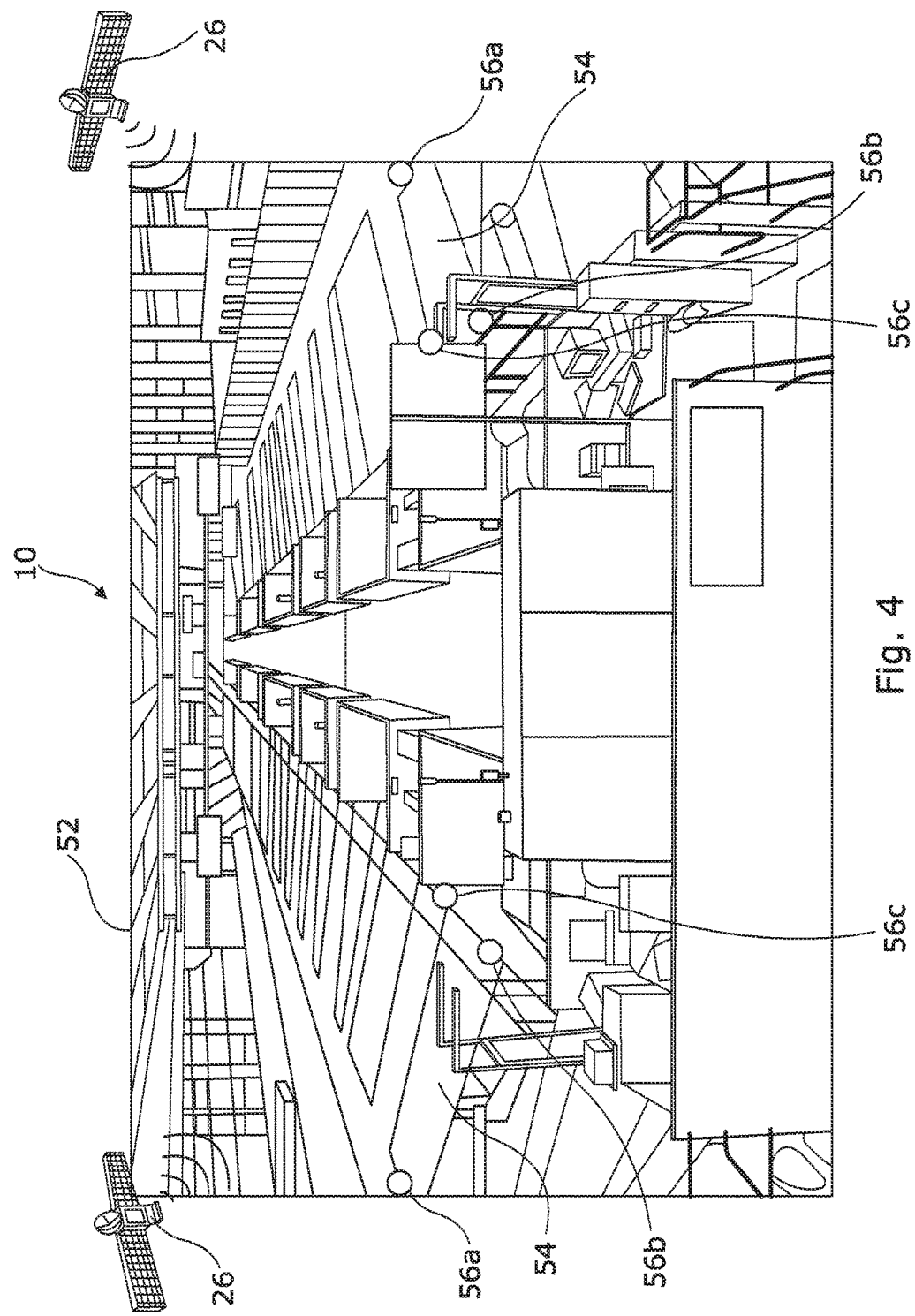

US 9,672,661 B2

DAMAGE DETECTION AND REPAIR SYSTEM AND METHOD USING ENHANCED GEOLOCATION

FIELD OF THE DISCLOSURE

The present disclosure generally relates to aircraft repair systems, and in particular relates to a damage detection and repair system using geolocation and digital mockup (DMU) models.

BACKGROUND OF THE INVENTION

Generally, a mobile device includes a Global Positioning System (GPS) that provides relative location and time information in all weather conditions. The GPS is well known in the navigation system art. Thus, the GPS is a widely used satellite-based navigation system comprising of a network of satellites broadcasting geographical coordinate information or signals to a GPS receiver. Based on the received coordinate information, the GPS receiver determines locations of surrounding objects and calculates velocity, altitude, travel time, and the like. Accuracy of such measurements depends on the errors of the GPS signals and the geometry recognized by the positions of the satellites relative to the mobile device.

When the GPS signals are unavailable, conventional geolocation systems installed in certain mobile devices use relevant information from cell towers to triangulate the device's approximate position. Certain geolocation systems use the GPS signals and the cell site triangulation in combination for identifying an accurate location of the mobile device. Since the mobile device is typically coupled to other devices via a wired or wireless communication link, the geolocation system can report the information to other users, and associate other surrounding locations to a current position of the mobile device, such that associated computing devices can send and receive positional and temporal information of the surrounding objects as the corresponding locations change in real time.

Conventionally, a damage detection and repair facility for aircraft and other vehicles and equipment uses preset requirements defined in working definitions or manuals as a set of rules. As the damage detection and repair facility examines conditions in an area surrounding the location at which the damage was detected, an extent of damage is determined, and an appropriate repair procedure is performed based on the set of rules.

However, the damage detection and repair preparation process typically involves various entities, including a customer, a Major Repair Organization (MRO), and other related third-party providers. Thus, it is difficult to communicate any detected damage to the various entities using only texts and inadequate images, which is prone to generating costly returns, mistakes, and delays. Moreover, although a Structure Repair Manual (SRM) and other informal documents are provided for describing various repair methods for the MRO, the SRM and similar documents have to be rechecked at each step of the repair process, resulting in a slow repair process.

Therefore, there is a need for developing an improved damage detection and repair system that is cost-effective and time-saving without generating substantial errors or delays during the damage detection and repair tasks.

SUMMARY OF THE INVENTION

Advantages are achieved by the present damage detection and repair system (or tool) which automatically provides an online or electronic damage report prefilled with aircraft information and at least one associated defect description having a digital mockup (DMU) model. An important aspect of the present damage detection and repair system is that the present system is used to provide a large scope of functions, such as localizing a region or zone of interest (ROI) in various mockup models, and performing accurate damage detections and preparation for repairs for the aircraft.

As described in greater detail below, each damage is initially photographed using an image-capturing device, such as a cellular phone equipped with a color camera, for identifying any damage to the aircraft. Depending on the number of lenses on the image-capturing device, two-dimensional (2D) or three-dimensional (3D) images are generated using a positional alteration method known in the art, such as a parallax technique.

The DMU model is automatically generated based on an aircraft drawing tree for selectively mapping out the damage to the aircraft relative to the positional information shown in the 2D or 3D images, such that associated replacement components of the aircraft are promptly ordered or prepared for repair. For example, since the coordinates of the image-capturing device in the overall landmark and the position of the aircraft in the global landmark are known, an aircraft identifier, such as a Manufacturer Serial Number (MSN), and a point of view to be considered in a theoretical or virtual coordinate system of the DMU can be deduced to generate the DMU model. As such, the repair and preparation time is significantly reduced, and the damage detection and repair quality is improved.

Another advantage of the present damage detection and repair system is that the online damage report provides immediate information about the detected damage and corresponding repair procedures having detailed descriptions about the damage and aircraft configuration using the DMU model. There is no need to recheck the aircraft configuration, or return the repair work to an initial inspector or originator for additional explanations because such information is provided and readily available in the online damage report. Also, any corresponding native drawings of the aircraft are automatically extracted from a database for viewing during the review of the online damage report.

In one embodiment, a damage detection and repair system is provided for performing a damage detection and repair preparation process, and includes an image-capturing device having at least one camera lens, a first positional sensor, and an orientation sensor relative to a global positioning system. At least two second positional sensors are provided for the object to detect a corresponding three-dimensional (3D) position and orientation of the object relative to the global positioning system. A location determination module determines a positional information of the damage based on signals received from the first positional sensor, the orientation sensor, and the second positional sensors. A 3D generation module retrieves a 3D digital mockup model for illustrating the damage to the object and associated parts needed for repairing the damage.

In another embodiment, a method for detecting damage of an object and repairing the damage is provided, and includes taking at least one photographic image of the damage to the object using an image-capturing device; receiving signals from a first positional sensor and an orientation sensor of the image-capturing device, and at least two second positional sensors provided for the object, to detect a corresponding three-dimensional (3D) position of the object relative to the image-capturing device; determining a positional information of the damage to the object based on the received signals; generating a 3D digital mockup (DMU) model of the object showing the damage based on a 3D drawing tree of the object, and the received signals; and illustrating the damage to the object and associated parts needed for repairing the damage on a display device in 3D computer graphics.

The foregoing and other aspects and features of the disclosure will become apparent to those of reasonable skill in the art from the following detailed description, as considered in conjunction with the accompanying drawings.

BRIEF DESCRIPTION OF THE DRAWINGS

FIG. 4 illustrates another exemplary practice of the present damage detection and repair system of FIG. 1 during a manufacturing process.

DETAILED DESCRIPTION OF THE PREFERRED EMBODIMENTS

Preferred embodiments of the present disclosure are described below by way of example only, with reference to the accompanying drawings. Further, the following description is merely exemplary in nature and is in no way intended to limit the disclosure, its application, or uses.

As used herein, the term "module," or "unit" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logic circuit, and/or other suitable components that provide the described functionality. Although children modules residing in their respective parent modules are shown, the broad teachings of the present system can be implemented in a variety of forms. Thus, while this disclosure includes particular examples and arrangements of the modules, the scope of the present system should not be so limited since other modifications will become apparent to the skilled practitioner.

Exemplary embodiments herein below are directed primarily to damage detection and repair systems. However, the present system can be implemented for other types of products or services, such as in a material processing or manufacturing field, and the like.

Figure 1:
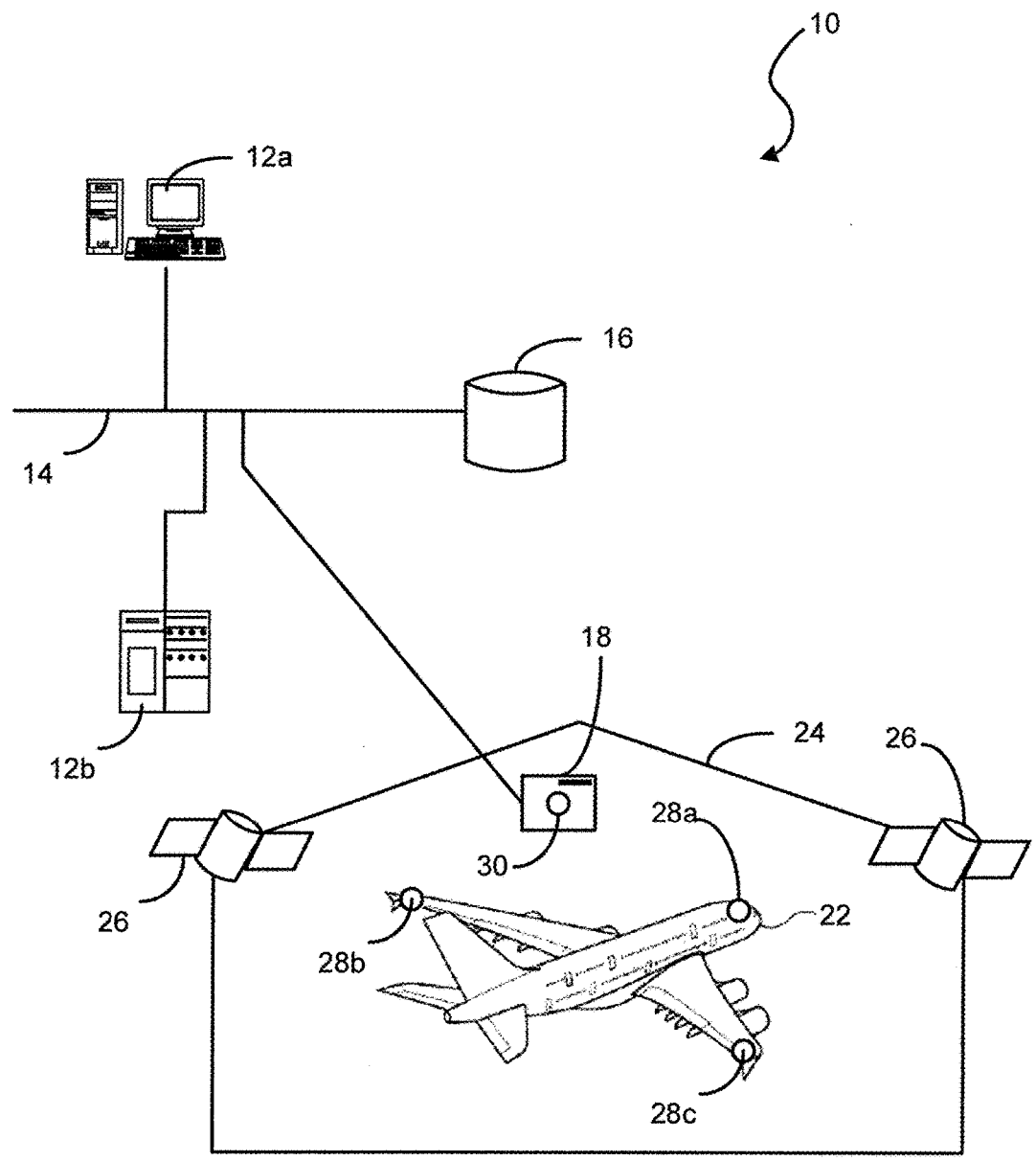
FIG. 1 illustrates an exemplary environment for the present damage detection and repair system in accordance with an embodiment of the present disclosure.
Figure 1A:
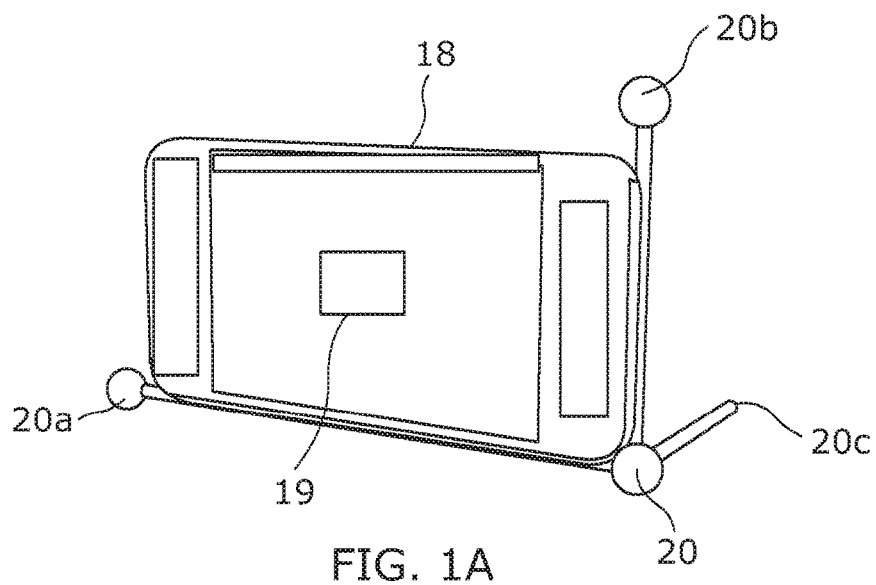
FIG. 1A is an exemplary image-capturing device having 3D positional and orientation sensors.

Referring now to FIGS. 1 and 1A, an exemplary damage detection and repair system for performing a damage detection and repair preparation process is schematically illustrated and generally designated 10. The present system 10 is coupled to at least one server or computing device 12a, 12b (including, for example, a database server and a video server), and is programmed to perform tasks and display relevant data for different functional units via a network 14.

It is contemplated that other suitable networks can be used, such as a corporate Intranet, a local area network (LAN) or a wide area network (WAN), and the like, using dial-in connections, cable modems, high-speed ISDN lines, and other types of communication methods known in the art. All relevant information can be stored in a database 16 for retrieval by the present system 10 or the computing device 12a, 12b (e.g., as a data storage device and/or a machine readable data storage medium carrying computer programs).

The present system 10 enables a maintenance crew member, such as an MRO damage report originator or a third-party inspector, to perform a damage detection process using an image-capturing device 18 having a 3D image mapping capability. As shown in FIG. 1A, it is preferred that the image-capturing device 18 includes a first positional sensor 19 configured to receive signals from the GPS satellites or cell towers, and an orientation sensor 20 configured for providing 3D orientation information, such as an X-axis 20a, a Y-axis 20b, and a Z-axis 20c, and configured for detecting corresponding 3D positions of the image-capturing device.

In FIG. 1A, the X-, Y-, and Z-axis 20a, 20b, 20c are shown in a fictitious manner for illustration purposes, and other suitable directional axis are contemplated to suit the application. It is also contemplated that the image-capturing device 18 includes a cellular phone or personal digital assistant, a desktop computer or server, a portable computing device, such as a laptop, a palm top, a tablet, and the like. Although the 3D configuration is described for the present system 10, a 2D configuration is also contemplated depending on different applications.

The image-capturing device 18 and other related devices, such as the computing devices 12a, 12b, are electrically coupled to each other via the network 14. Any type of computer network having a collection of computers and other hardware interconnected by communication channels is contemplated, such as the Internet, Ethernet, LAN, GAN, Cloud, and the like, as known in the art.

As an example only, when an object, such as an aircraft 22, is stored in a hangar 24 for corrective maintenance, the maintenance crew member takes a photographic image of the damage to the aircraft for performing a subsequent repair based on the image. During the damage detection process, the image-capturing device 18 receives signals from a plurality of GPS sensors 26 either directly or indirectly via the network 14.

More specifically, the GPS sensors 26 are installed at selected locations, such as a roof level of the hangar 24 (e.g., at two upper opposite corners), so that the GPS sensors can generate adequate signals or coordinates using the space-based satellite-like navigation system and communicate with the server 12a, so that the 3D position and reference of any device are accessible in the field of view. Each aircraft 22 includes at least three second positional sensors 28a, 28b, 28c configured for detecting corresponding 3D positions of the aircraft relative to the GPS sensors 26 disposed in the hangar 24.

For example, a first aircraft positional sensor 28a is disposed on a nose of the aircraft 22, and second and third aircraft positional sensors 28b, 28c are each disposed on a wing tip of the aircraft based on an aircraft axis system. An accurate position of each aircraft positional sensor 28a, 28b, 28c is determined based on a hangar reference axis system, for example, relative to the hangar position of the aircraft 22, such that the associated aircraft identifier, such as the MSN, is known in 3D in real time. It is contemplated that the hangar reference axis system is known worldwide, thereby allowing to generate a global positional information of the aircraft 22.

Alternatively, when the GPS signals are unavailable, an accelerometer of the image-capturing device 18 is used to determine the accurate position of the aircraft 22. For example, due to a treacherous weather condition or an unfavorable roof structure of the hangar 24, the GPS signals cannot be received by the image-capturing device 18.

However, an instant acceleration in three directions (e.g., X-axis, Y-axis, and Z-axis) coupled with the instant orientation can calculate the accurate position of the image-capturing device 18, and further determine the position of the aircraft 22 by performing numerical integration on a path travelled by the image-capturing device based on a last-known GPS signal. Other suitable inertial navigation systems using computer and motion sensors are contemplated for determining relative position, orientation, and velocity of the device without need for external references.

Thus, when the photographic image of the damage to the aircraft 22 is taken, the information related to a 3D position and orientation of the image-capturing device 18 is sent to the computing device 12a, 12b via the network 14, such that a 3D mapping of the damage is performed. It is contemplated that the image-capturing device 18 has at least one camera lens 30, but at least two lenses are preferred (e.g., three lenses) for generating a 3D image of the damage to the aircraft 22.

This allows an automatic 3D identification of the damage or defect, including its size, perimeter, area, depth, and the like. In practice, at least two photographic images are taken and compared to generate a 3D mesh of the damage using a positional alteration method, such as the parallax technique. This 3D image and 3D mesh are included in the online damage report, and viewed by a repair crew member during a repair preparation process.

Referring now to FIGS. 1, 1A, 2 and 2A, also included in the present system 10 is a control module (CM) 32, which regulates and controls operation of the system. In general, the CM 32 allows the maintenance and repair crew members to access 3D image information of the damage to the aircraft 22. It is contemplated that the CM 32 is electronically connected to the network 14 to communicate not only with the computing devices 12a, 12b, but also with a plurality of ancillary components, such as a printing device and a display device, of the present system.

It is contemplated that the CM 32 is installed either in the computing device 12a, 12b, the image-capturing device 18, or in a separate computing environment, such as a third-party service provider, a cloud computing environment, and the like. In a preferred embodiment, all relevant information is stored in the database 16, e.g., as a data storage device and/or a machine readable data storage medium carrying computer programs, for retrieval by the CM 32 and its children modules as desired.

For example, the CM 32 includes an interface module 34 for providing an interface between the CM 32, the database 16, and the network 14. The interface module 34 controls operation of, for example, the computing devices 12a, 12b, the image-capturing device 18, the network 14, and other related system devices, services, and applications. The other devices, services, and applications may include, but are not limited to, one or more software or hardware components, etc. The interface module 34 also receives signals, e.g., GPS signals, which are communicated to the respective modules, such as the CM 32, and its children modules.

It is preferred that as one of the children modules, the CM 32 includes a location determination module 36 that determines a positional information of the damage to the aircraft 22 based on signals received from the first positional sensor 19 and the orientation sensor 20 of the image-capturing device 18, the GPS sensors 26 of the hangar 24, and the positional sensors 28a, 28b, 28c of the aircraft. Thus, a precise location of the aircraft 22 is determined based on the received signals. As discussed above, the 3D mapping of the damage is performed by the location determination module 36 based on the received signals using the positional alteration method, such as the parallax technique. Other geolocation methods are also contemplated to suit the application.

Figure 2A:
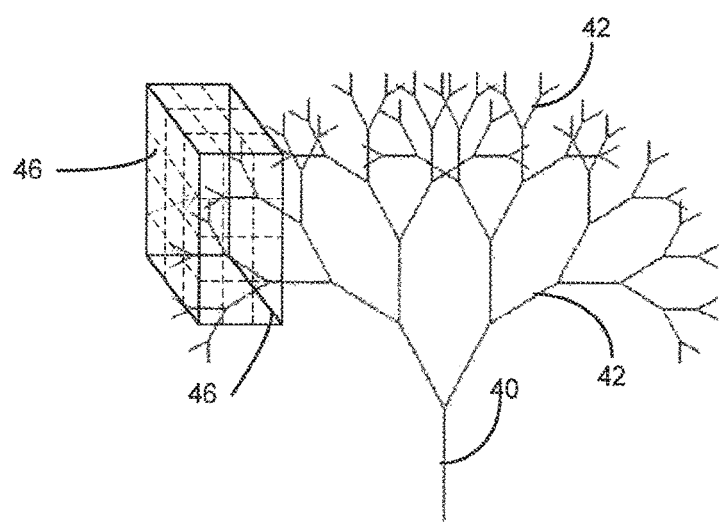
FIG. 2A illustrates an exemplary aircraft drawing tree featuring a 3D spatial boxing method.
Figure 2:
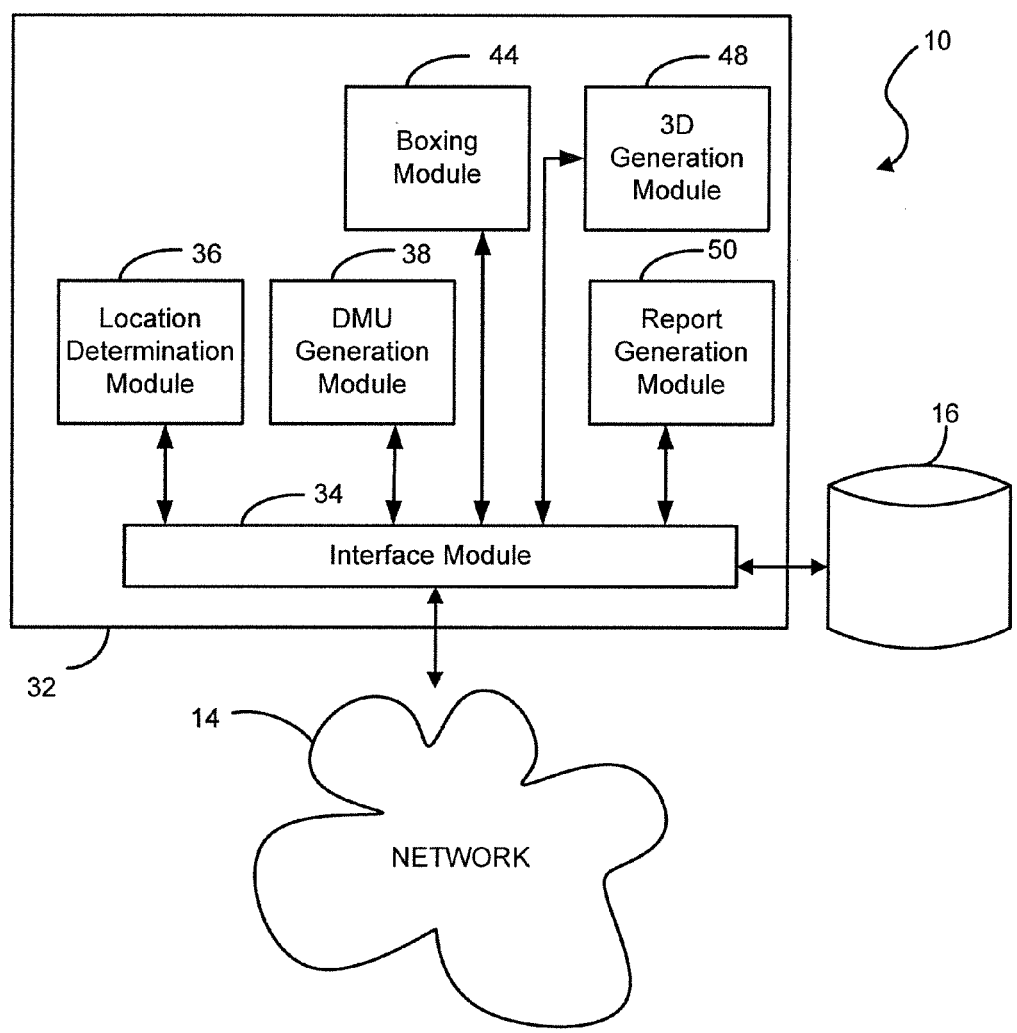
FIG. 2 is a functional block diagram of the present damage detection and repair system in accordance with an embodiment of the present disclosure.

Also included in the CM 32 is a DMU generation module 38 that retrieves and generates a DMU model of the aircraft 22 showing the damage based on a 3D drawing tree 40 (FIG. 2A) of the aircraft and the received signals. As illustrated in FIG. 2A, in certain cases, it is difficult to identify aircraft components or parts related to the damage when a plurality of branches 42 of the tree 40 are intertwined together. However, as a post treatment of the DMU model, each aircraft part is defined by a perimeter or extent of the branches 42 of the tree 40, such that the part can be readily identified by employing a 3D spatial boxing technique or method.

A boxing module 44 is included in the CM 32 to perform the 3D spatial boxing method, which refers to dividing the 3D aircraft drawing tree 40 into a plurality of 3D image boxes or cubes 46 (FIG. 2A), such that the intertwined branches 42 of the tree 40 are readily viewed in different angles. For example, each 3D image box or cube 46 can be manipulated (e.g., being rotated, tessellated, or removed from the tree 40) to assess the damage based on a predefined mesh system having a predetermined configuration. It is contemplated that a size of each mesh unit is variable and one of more mesh units are combinable or dividable to suit different applications.

In a preferred embodiment, each image box 46 is indexed and has a predetermined width, height and depth, having square or rectangular outer planes. However, other geometric configurations, such as oval, circular, cylindrical, and the like, are contemplated to suit the application. Further, a size of each image box 46 is variable depending on different applications. It is contemplated that each box 46 can be further subdivided into lower-level boxes or cubes, and two or more cubes are combinable as one unit. In this configuration, identifying the aircraft components related to the damage is faster and easier for the maintenance and repair crew members.

A 3D generation module 48 is provided in the CM 32 that generates a 3D DMU model for illustrating the damage to the aircraft 22 along with the associated aircraft components or parts needed for repairing the aircraft. For example, the rotated and/or tessellated 3D image boxes 46 are displayed on the display device, using a computer graphic language, such as an Extensible Markup Language (XML)-based file format and a Virtual Reality Modeling Language (VRML). Other suitable computer animation techniques, such as vector graphics and full motion videos, are contemplated for representing 3D computer graphics.

A report generation module 50 of the CM 32 generates an online or electronic damage report based on the 3D DMU model. In a preferred embodiment, the damage report includes the MSN of the aircraft 22, part numbers of the aircraft components related to the damage, and the 3D DMU model of a damaged area of the aircraft. Optionally, the original 3D DMU model of the aircraft 22 can be superimposed with the 3D picture or 3D mesh of the damaged area and can be compared concurrently while superimposed on top of each other. Thus, it is advantageous that faster and easier damage detection and repair procedures are performed for the crew members.

It is preferred that an online electronic SRM link is included in the damage report for proposing at least one repair procedure for the detected damage to the aircraft 22. Further, other ancillary instructions, such as repair approval and capacity of the MRO, are also included in the damage report. Depending on the chosen repair procedure, the damage report can be issued directly to the MRO, or to another maintenance and repair officer for further review.

Figure 3:
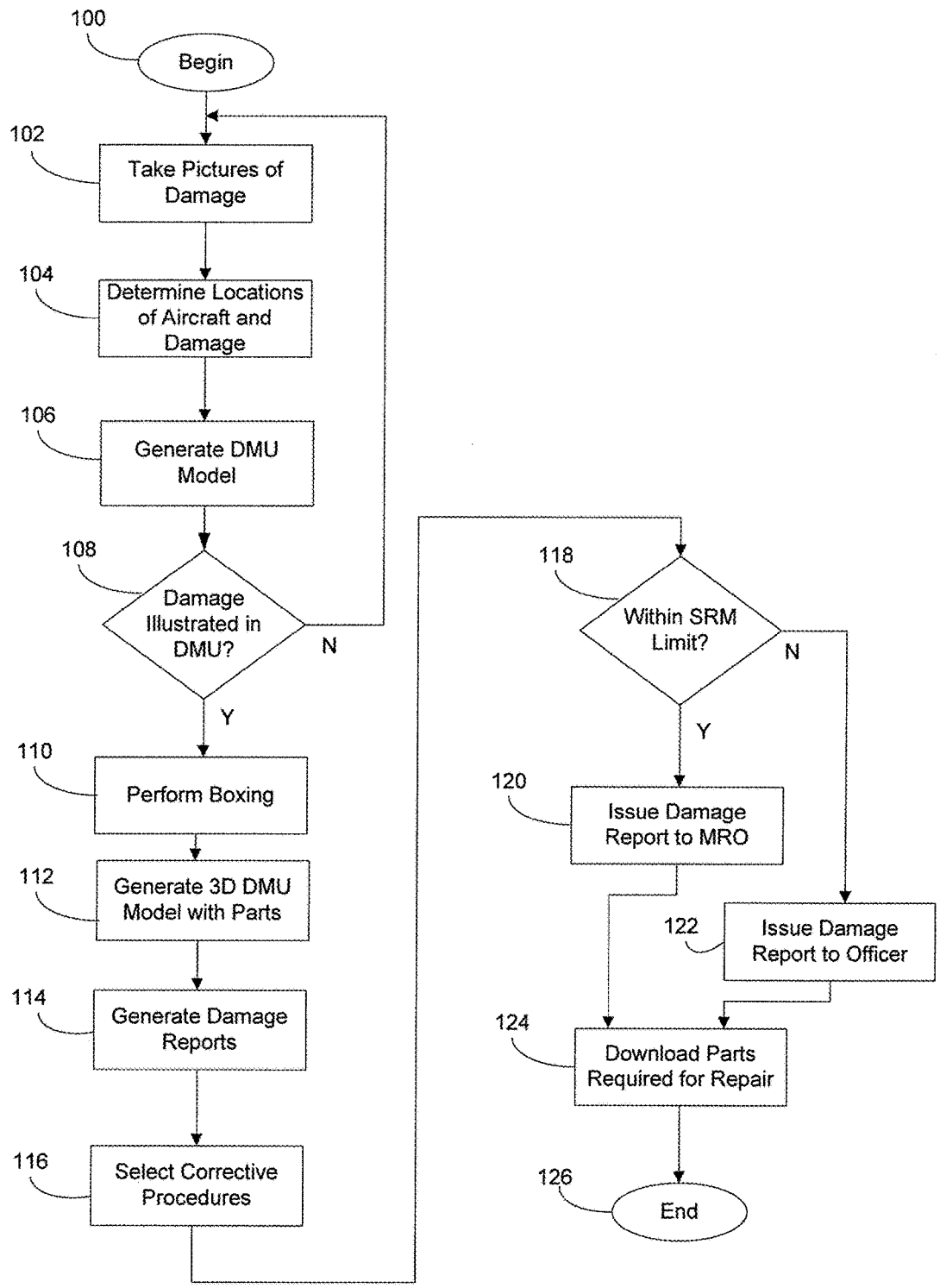
FIG. 3 illustrates an exemplary damage detection and repair method in accordance with an embodiment of the present disclosure.

Referring now to FIG. 3, an exemplary method is illustrated for performing the damage detection and repair preparation process using the present system 10. Although the following steps are primarily described with respect to the embodiments of FIGS. 1, 1A, 2, and 2A, it should be understood that the steps within the method may be modified and executed in a different order or sequence without altering the principles of the present disclosure.

The method begins at step 100. In step 102, the maintenance crew member takes at least one photographic image of the damaged area of the aircraft 22, using the image-capturing device 18 for performing the subsequent repair based on the image. During the damage detection process, the image-capturing device 18 receives an orientation signal from the orientation sensor 20 having 3D orientation information based on the X-axis, Y-axis, and Z-axis 20a, 20b, 20c of the image-capturing device, the GPS sensors 26 of the hangar 24, via the network 14, and transmits the signals to the interface module 34. Thus, it is contemplated that the position of the aircraft 22 is calculated independently of the movement of the image-capturing device 18. Further, the position of the aircraft 22 is monitored in real time by the present system 10.

In step 104, the location determination module 36 receives the signals from the interface module 34, and determines the positional information of the damaged area of the aircraft 22 based on the received positional signals. Also, the precise location of the aircraft 22 is determined based on at least two of the received positional signals. Based on the location of the aircraft 22, the location determination module 36 retrieves a specific aircraft information from the database 16, such as the MSN of the aircraft 22, the part numbers of the damaged parts, and related repair programs or procedures.

In step 106, the DMU generation module 38 generates the DMU model of the aircraft 22 showing the detected damage based on the 3D aircraft drawing tree 40 and the received signals. As discussed above, the aircraft parts are defined by the perimeters or extents of the branches 42 of the tree 40 for subsequent identification.

In step 108, when the damage is adequately illustrated in the DMU model of the aircraft 22, control proceeds to step 110. Otherwise, control returns to step 102. For example, the maintenance crew member reviews the DMU model of the aircraft 22 to determine whether the damage is properly shown in the DMU model. Otherwise, the maintenance crew member retakes the photographic image of the damage to the aircraft 22, using the image-capturing device 18.

In step 110, as discussed above, the aircraft components or parts related to the damage are identified by employing the 3D spatial boxing method. The boxing module 44 performs the 3D spatial boxing method on the DMU model, and divides the 3D aircraft drawing tree 40 into the 3D image boxes or cubes 46. Only the image boxes or cubes 46 related to the damage are selected for review, and the aircraft parts associated with the selected image boxes are downloaded from the database 16.

In step 112, the 3D generation module 48 generates the 3D DMU model for illustrating the damage to the aircraft 22 along with the associated aircraft components or parts for repair. Because only the parts related to the damage are shown in the DMU model, a response time for the repair preparation process is substantially reduced. For example, the 3D generation module 48 retrieves the 3D DMU model representing an image before the damage, and generates a 3D mesh representing an image after the damage. The 3D DMU model and the 3D mesh are then compared or superimposed to examine the damage to the aircraft 22.

In step 114, the report generation module 50 generates the online damage report having at least one proposed repair procedure based on the 3D DMU model. The damage report includes the MSN of the aircraft 22, the part numbers of the aircraft parts related to the damage, and the 3D DMU model of the damage area. Since all information related to the damage is automatically included in the damage report as Uniform Resource Locator (URL) links or embedded data, there is no need to recheck or download the information by the maintenance crew member for the subsequent repair preparation process.

In step 116, the damage report includes the electronic SRM link for proposing at least one repair procedures for the detected damage to the aircraft 22. The MRO or other repair crew members can select one or more repair procedures from the SRM.

In step 118, when the selected repair procedure is within predetermined repair limits defined by the SRM associated with the aircraft 22, control proceeds to step 120. Otherwise, control proceeds to step 122. In step 120, for example, when the selected repair procedure is approved to be performed by the MRO, the damage report is issued to the MRO repair crew member. Otherwise, in step 122, when the selected repair procedure is not approved to be performed by the MRO, the damage report is issued to another Non-MRO maintenance and repair officer for further review.

In step 124, the report generation module 50 automatically downloads all repair parts related to the damage into a virtual folder, such that the repair crew member can open the folder, and promptly identify and retrieve the parts in preparation of the repair. The method ends at step 126.

Referring now to FIGS. 1, 1A, 2, 2A, and 4, another variant practice of the present damage detection and repair system 10 is illustrated. Components shared with the present system 10 are designated with identical reference numbers. In one embodiment, the present system 10 is used to detect the damage on the aircraft parts or components during the manufacturing process of the aircraft 22. As with the hanger 24, the GPS sensors 26 are installed at the roof level of a manufacturing plant 52 to generate the signals or coordinates.

Each aircraft component or part 54 (e.g., a wing) or supporting tool is equipped with at least three third positional sensors, such as an X-axis sensor 56a, a Y-axis sensor 56b, and a Z-axis sensor 56c, configured for detecting corresponding 3D positions of the component based on the aircraft axis system. Thus, as described above, the MSN of the aircraft 22, and the 3D positions of the components 54 are automatically determined in real time. Also, a sequence phase of the manufacturing process of the aircraft 22 can be retrieved from the database 16 based on the MSN.

When an inspector at the plant 52 detects a damaged component 54, and takes a photographic image of the damaged component, the corresponding 3D position and orientation signals of the image-capturing device 18 are transmitted to the interface module 34. The 3D identification of the damage or defect of the component 54 is automatically performed by the location determination module 36.

Then, the DMU model of the component 54 is generated by the DMU generation module 38 based on the 3D aircraft drawing tree 40 and the signals. After performing the 3D spatial boxing method, only the parts related to the damage to the component 54 are identified and shown in the DMU model by the 3D generation module 48.

An online or electronic inspector document is generated by the report generation module 50 based on the 3D DMU model, which includes at least one of the MSN, the part numbers, the 3D DMU models, and other related repair documents, as discussed above. Thus, the present system 10 can be implemented for other types of products or services, such as in a material processing or manufacturing field, and the like.

While at least one exemplary embodiment of the present invention has been shown and described, it should be understood that modifications, substitutions and alternatives may be apparent to one of ordinary skill in the art and can be made without departing from the scope of the invention described herein. This application is intended to cover any adaptations or variations of the specific embodiments discussed herein. In addition, in this application, the terms "comprise" or "comprising" do not exclude other elements or steps, and the terms "a" or "one" do not exclude a plural number. Furthermore, characteristics or steps which have been described with reference to one of the above exemplary embodiments may also be used in combination with other characteristics or steps of other exemplary embodiments described above.

What is claimed is:

1. A damage detection and repair system to detecting damage of an object and preparing for repairing the damage, comprising:
    an image-capturing device having at least one camera lens, a first positional sensor, and an orientation sensor;
    at least three second positional sensors provided for the object to detect a corresponding three-dimensional (3D) position of the object relative to the image-capturing device;
    and a processor configured to:
    determine a positional information of the damage of the object based on signals received from the first positional sensor, the orientation sensor, and the second positional sensors; and
    generate a 3D digital mockup (DMU) model for illustrating the damage of the object and associated parts needed for repairing the damage,
    wherein the object is an aircraft, and the at least three second positional sensors include a nose sensor disposed on a nose of the aircraft and two wing sensors, each wing sensor disposed on a wing tip of the aircraft.

2. The damage detection and repair system of claim 1, wherein the processor is further configured to retrieve a 3D DMU model representing an image before the damage, and generate a 3D mesh representing an image after the damage.

3. The damage detection and repair system of claim 2, wherein the 3D DMU model and the 3D mesh are superimposed for concurrent comparison with each other.

4. The damage detection and repair system of claim 1, wherein the processor is further configured to generate an electronic damage report based on the 3D DMU model of a damaged area of the object.

5. The damage detection and repair system of claim 4, wherein the damage report includes at least one of an identifier of the object, part numbers of the associated parts used for repairing the damage, and the 3D DMU model.

6. The damage detection and repair system of claim 4, wherein the damage report includes an online link directing to an electronic repair manual having at least one proposed repair procedure for the detected damage.

7. The damage detection and repair system of claim 1, wherein the processor is further configured to generate a DMU model of the object showing the damage based on a 3D drawing tree of the object and the signals.

8. The damage detection and repair system of claim 7, wherein each part of the object is defined by a perimeter or extent of a plurality of branches of the 3D drawing tree by employing a 3D spatial boxing method.

9. The damage detection and repair system of claim 7, wherein the processor is further configured to divide the 3D drawing tree into a plurality of 3D image boxes, such that each 3D image box is manipulated to assess the damage based on a predefined mesh system having a predetermined geometric configuration.

10. The damage detection and repair system of claim 9, wherein each 3D image box is indexed and has a predetermined configuration.

11. The damage detection and repair system of claim 9, wherein each 3D image box is dividable into lower-level boxes, and combinable with other 3D image boxes as one unit.

12. The damage detection and repair system of claim 1, wherein the orientation sensor includes an X-axis, a Y-axis, and a Z-axis.

13. The damage detection and repair system of claim 1, wherein the image-capturing device includes an accelerometer to determine the 3D position of the object.

14. The damage detection and repair system of claim 1, wherein the processor is further configured to provide an interface between the image capturing device, the first and second positional sensors, and associated modules of the system via a network.

15. A method for detecting damage of an object and preparing for repairing the damage, comprising:
    taking at least one photographic image of the damage of the object using an image-capturing device;
    receiving signals from a first positional sensor and an orientation sensor of the image-capturing device, and at least three second positional sensors provided for the object, to determine a corresponding three-dimensional (3D) position of the object relative to the image-capturing device;
    determining a positional information of the damage of the object based on the received signals;
    generating a 3D digital mockup (DMU) model of the object showing the damage based on a 3D drawing tree of the object, and the received signals; and
    illustrating the damage of the object and associated parts used for repairing the damage on a display device in 3D computer graphics.

16. The method of claim 15, further comprising performing a 3D spatial boxing method on the 3D DMU model, and dividing the 3D drawing tree into a plurality of 3D image boxes.

17. The method of claim 15, further comprising generating the 3D DMU model having associated repair parts for the object.

18. The method of claim 15, further comprising generating an electronic damage report having at least one proposed repair procedure based on the 3D DMU model.

19. The method of claim 18, further comprising issuing the damage report based on predetermined repair limits defined by a repair manual associated with the object.

20. A damage detection and repair system for detecting damage of an object and preparing for repairing the damage, comprising:
- an image-capturing device having at least one camera lens, a first positional sensor, and an orientation sensor;
- at least three second positional sensors provided for the object to detect a corresponding three-dimensional (3D) position of the object relative to the image-capturing device;
- and a processor configured to:
- determine a positional information of the damage of the object based on signals received from the first positional sensor, the orientation sensor, and the second positional sensors;
- generate a 3D digital mockup (DMU) model for illustrating the damage of the object and associated parts needed for repairing the damage; and
- generate a DMU model of the object showing the damage based on a 3D drawing tree of the object and the signals.

* * * * *